United States Patent [19]

Moss et al.

[11] Patent Number: 5,135,855

[45] Date of Patent: * Aug. 4, 1992

[54] RAPID, VERSATILE AND SIMPLE SYSTEM FOR EXPRESSING GENES IN EUKARYOTIC CELLS

[75] Inventors: Bernard Moss, Bethesda; Thomas Fuerst, Gaithersburg; Orna Elroy-Stein, Rockville, all of Md.

[73] Assignee: The United States of America as represented by the Department of Health and Human Services, Bethesda, Md.

[*] Notice: The portion of the term of this patent subsequent to Jun. 30, 2009 has been disclaimed.

[21] Appl. No.: 376,687

[22] Filed: Jul. 7, 1989

Related U.S. Application Data

[63] Continuation-in-part of Ser. No. 905,253, Sep. 3, 1986, abandoned.

[51] Int. Cl.$^5$ .................. C12N 15/00; C12P 21/00
[52] U.S. Cl. .................. 435/69.1; 935/34; 935/70; 935/60; 935/36
[58] Field of Search .............. 435/69.1, 320, 235, 435/172.3; 935/27, 32, 34, 60

[56] References Cited

U.S. PATENT DOCUMENTS 4,937,190  6/1990  Palmenberg et al. .......... 435/69.1

Primary Examiner—Richard A. Schwartz
Assistant Examiner—S. L. Nolan
Attorney, Agent, or Firm—Foley & Lardner

[57] ABSTRACT

An efficient, versatile and simple expression system which confers cap-independent translation to prokaryotic RNAs in eukaryotic cells has been described. The utility of recombinant vaccinia virus for this purpose has been illustrated.

12 Claims, 5 Drawing Sheets

FIG. 1A
pT7CAT

FIG. 1B
pT7EMCAT

RAPID, VERSATILE AND SIMPLE SYSTEM FOR EXPRESSING GENES IN EUKARYOTIC CELLS

This is a continuation-in-part of application Ser. No. 905,253 filed Sep. 3, 1986, now abandoned which is incorporated herein by reference.

The parent application (Ser. No. 905,253) relates to the expression of foreign genes in eukaryotic cells and organisms and especially relates to the use of prokaryotic genes, e.g., the genes of bacteria and viruses in eukaryotic cells, e.g., the cells of higher organisms, particularly mammals. However, the level of protein synthesis achieved with the expression system disclosed in the parent application is rather limited. The present invention extends the basic system described in the parent application to provide an improved, rapid and versatile system with substantially higher level of protein synthesis.

SUMMARY OF THE INVENTION

An object of the present invention is to provide an efficient expression system which confers cap-independent translation to RNAs in eukaryotic cells, particularly when a prokaryotic transcription system is used in eukaryotic cells.

An additional object of the present invention is to provide a method for controlled expression of toxic genes.

Other objects and advantages will become evident from the following detailed description of the invention.

BRIEF DESCRIPTION OF THE DRAWINGS

These and other objects, features and many of the attendant advantages of the invention will be better understood upon a reading of the following detailed description when considered in connection with the accompanying drawings wherein:

FIG. 2 shows the results of time course study of CAT synthesis during vaccinia virus infection. CV-1 cell monolayers were infected with 20 PFU per cell of wild-type vaccinia virus (lane 9), or co-infected with vTF7-3 and vT7CAT (lanes 1, 2, 5, 6, 10, 11), or with vTF7-3 and vT7EMCAT (lanes 3, 4, 7, 8, 12, 13) at a multiplicity of 10 PFU per cell of each virus. At 2, 7 and 24 hr after infection, cells were starved for methionine for 20 min and then were pulse-labeled with [$^{35}$S]methionine for 30 min. Starvation and pulse labelling were done in isotonic (lanes 1, 3, 5, 7, 9, 10, 12) or hypertonic (190 mM NaCl) (lanes 2, 4, 6, 8, 11, 13) conditions. Cell lysates were prepared and equal volumes (corresponding to $2 \times 10^5$ cells) were loaded in each lane of a 10% NaDodSO$_4$-polyacrylamide gel. Following electrophoresis, the gel was processed for fluorography. The arrow identifies the CAT protein.

DETAILED DESCRIPTION OF THE INVENTION

Figure 1A:
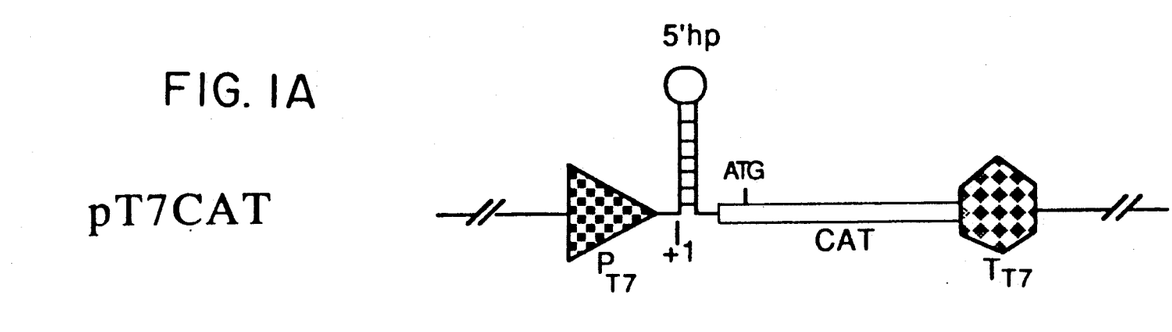
FIGS. 1A and B show a schematic structure of expression cassettes in accordance with the present invention. Abbreviations: $P_{T7}$, bacteriophage T7 010 promoter from $-23$ to $+1$, 5'hp, nucleotides $+1$ to $+26$ downstream of the 010 promoter and capable of forming a hairpin or stem-loop structure; $T_{T7}$, bacteriophage T7 010 termination sequence; EMC, nucleotides 163 to 746 of the EMCV UTR.
Figure 1B:
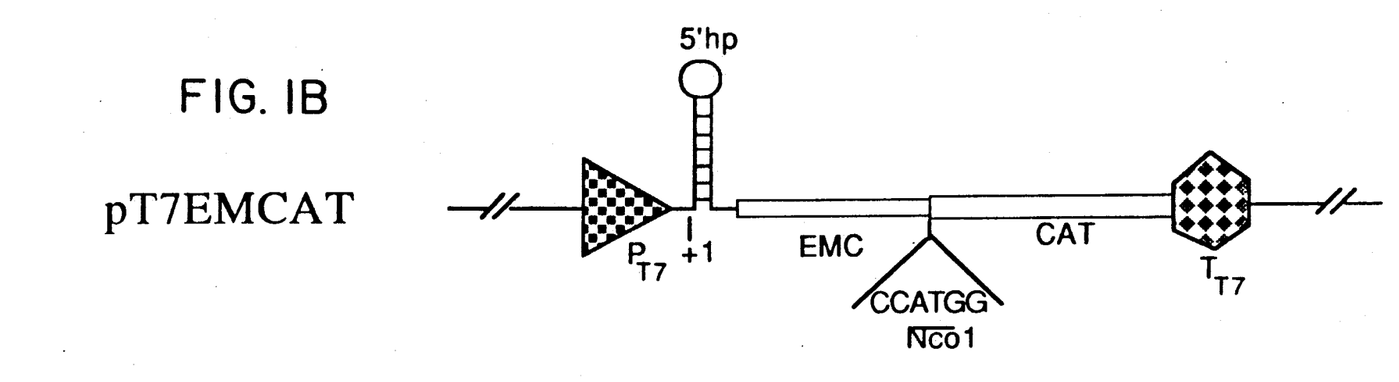

The above and various other objects and advantages of the present invention are achieved by an expression system, wherein the vector is a DNA based cytoplasmic virus, RNA polymerase and promoter are from a DNA bacteriophage and the ribosome binding site is from an RNA virus. The preferred embodiment comprises a recombinant vaccinia virus constructed to include a T7 promoter, an encephalomyocarditis virus (ECMV) untranslated region (UTR), and a T7 promoter regulated gene for a protein desired to be expressed, as illustrated in FIG. 1. However, it should be noted that the untranslated region that confers cap independent translation may be from sources other than EMCV including related viruses such as poliovirus and mengovirus and from unrelated viruses such as adenovirus and the like. The examples provided herein are only illustrative and not limiting. For instance, following the teachings of the present invention, other prokaryotic transcription systems such as bacteriophage SP6, T3 and GH1 could be employed for expression in eukaryotic cells.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference. Unless mentioned otherwise, the techniques employed or contemplated herein are standard methodologies well known to one of ordinary skill in the art. The materials, methods and examples are illustrative only and not limiting.

MATERIALS AND METHODS

MATERIALS

Restriction endonuclease were obtained from New England Biolabs, Bethesda Research Laboratories or Boehringer Mannheim. $m^7GpppG$, $GpppG$, and $m^7GDP$ were obtained from Pharmacia and T7 RNA polymerase and rabbit reticulocyte lysate from Promega Biotec.

Viruses and cells

Vaccinia virus (strain WR) was originally obtained from American Type Culture Collection. Viruses were purified as reported previously (Fuerst et al, 1986, *Proc. Natl. Acad. Sci USA* 83, 8122-8126). HeLa S-3 cells were grown in suspension in Eagle's minimal essential medium supplemented with 5% horse serum. CV-1 monkey kidney cells were propagated as monolayers in Dulbecco's modified Eagle's medium containing 10% fetal bovine serum. Cells were infected as described previously (Fuerst et al, 1987, *Mol. Cell Biol.* 7, 2538-2544; Fuerst et al, 1989, *J. Mol. Biol.* 206:333-348).

Plasmid constructions

A 0.6 kilobasepair (kbp) EcoR1-Ball EMC fragment from pE5LVPO (Parks et al, 1986, *J Virol.* 60, 376-384) containing nucleotides 163 to 746 of the EMCV UTR was inserted into the blunted BamH1 site of plasmid vector pAR2529 (Rosenberg et al, 1987, *Gene* 56, 125-135 to generate pTF7.25EMC-1. The CAT coding sequence was isolated from pTF7CAT-1 (Fuerst et al, supra), as 0.8 kbp Taq¹ fragment and using BamH1 linkers was inserted into the BamH1 site of pUC18 to generate the plasmid pUC18CAT-1. The 0.8 kbp BamH1 CAT fragment was then isolated from pUC1-8CAT-1 and inserted into a unique BamH1 site of plasmid pTF7.25EMC-1 downstream of the major translation start site of EMC, to form plasmid pTF7.25EMCAT-1. This resulted in placing the CAT translation start site in frame with the EMC major start signal separated by 12 amino acid residues. The coding frame of CAT was placed immediately downstream of EMC start codon by site directed mutagenesis. The sequence immediately flanking the initiating EMC ATG was changed to 5'-EMC ... GATAATACCATGGAG ... CAT-3', which provides a unique Nco1 site. An Nco1 site contained within the CAT gene was removed by placing a silent mutation within the coding sequence. The mutagenized EMC CAT cassette was then isolated as a 0.82 kbp BamH1-Kpn1 fragment and inserted into the corresponding site in plasmid pTF7.25EMCAT-1 to create pTF7.25EMCAT-20. For simplicity pTF7.25EMCAT-20 and pTF7CAT-1 will be referred to as pT7EMCAT and pT7CAT, respectively.

A deposit of pT7EMCAT plasmid has been made at the ATCC, Rockville, MD. on Jul. 7, 1989 under the accession number 68045. The deposit shall be viably maintained, replacing if it becomes non-viable during the life of the patent, for a period of 30 years from the date of the deposit, or for 5 years from the last date of request for a sample of the deposit, whichever is longer, and upon issuance of the patent made available to the public without restriction in accordance with the provisions of the law. The Commissioner of Patents and Trademarks, upon request, shall have access to the deposit.

Vaccinia virus insertion vectors were prepared by excising the complete T7 promoter-target gene-T7 terminator cassettes as BglII fragments, blunting the ends and inserting into the blunted EcoR1 site of pGS50 (Fuerst et al, supra). This resulted in flanking the target gene cassettes with vaccinia virus thymidine kinase (TK) sequences used for homologous recombination. Recombination into the genome of vaccinia virus and the isolation of recombinant virus was carried out as described by Mackett et al, 1984, *J. Virol.* 49:857-864.

In Vitro Transcription

Plasmids were digested with BamH1 to release the T7 transcription unit as a linear DNA fragment. Transcription was carried out as recommended by Promega Biotec except that the GTP concentration was 0.05 mM and $m^7GpppG$ or $GpppG$ were added at concentrations of 0.5 mM. A portion of each transcription reaction mixture contained [alpha-$^{32}p$]UTP and the products were analyzed on a 0.4% polyacrylamide-urea gel to ascertain the presence of a single appropriate size major RNA species. Yields of transcripts were calculated from the absorbance at 260 nm following 2 rounds of spin filtration through Sephadex G-50 columns and 2 ethanol precipitations.

In Vitro Translation

RNA was translated in a rabbit reticulocyte lysate as described by Promega Biotec except that the final reaction volume was 12.5 $\mu$l; 0.1 mM $m^7GDP$ was used as a specific inhibitor of cap-dependent translation when indicated. The final concentrations of in vitro or in vivo made RNA in the translation reaction mixture were 8 nM or 80 ng/$\mu$l, respectively. Following translation, 25 $\mu$l of a solution containing 9M urea, 75 mM EDTA, 1.5 mM phenylmethyl sulfonyl fluoride, 8000 U/ml RNase T1, and 40 $\mu$g/ml RNase A were added for a further 30 min incubation at 30° C. to digest aminoacylated tRNA. A 10 $\mu$l sample of the translation mixture was dissociated with NaDodSO$_4$ and mercaptoethanol and analyzed by 15% polyacrylamide gel electrophoresis as described by Pelletier et al (1988, *Mol. Cell. Biol.* 8, 1103-1112).

RNA Preparation and Analysis

HeLa S-3 cells (5 × 10⁸) were coinfected with recombinant vaccinia viruses as described by Fuerst et al, supra; 12 hr later, extracts were prepared and sedimented on sucrose gradients as described by Katze et al (1986, *J. Virol.* 60:1027-1039). Portions of each fraction were used for absorbance measurements at 260 nm and for slot blot hybridization (White et al, 1982, *J. Biol. Chem* 157, 8569-8572) with a [$^{32}p$]-labeled CAT DNA probe. Polyribosome and free RNA-containing fractions were pooled separately, ethanol precipitated and resuspended in 4 ml of 0.1M Tris-HCl (pH 7.5)-12 mM EDTA-0.15M NaCl-0.1% NaDodSO$_4$. Proteinase K was added to a final concentration of 50 μg/ml and the mixture was incubated for 30 min at 37° C. RNA was extracted 3 times with phenol-chloroform and twice with chloroform, ethanol precipitated, washed with 70% ethanol and resuspended in water. A portion of each sample was analyzed for size by electrophoresis on a 1.4% agarose-formaldehyde gel. The RNA was transferred to a nitrocellulose membrane and hybridized to a [$^{32}$p]-labeled CAT DNA probe.

CAT Assay

CAT was measured as described by Shaw (1975, Methods in Enzymology 43, 737-748), with modifications. Confluent CV-1 cells in a 6-wells plate were coinfected and grown with minimum essential medium without Phenol Red (Quality Biological, Inc.) and supplemented with 2.5% fetal bovine serum. At 24 hr after infection, the cells and medium were collected and lysis was achieved by addition of NaDodSO$_4$ and chloroform to 0.0005% and 1%, respectively. Samples (5-20 μl) were transferred to a 96-wells plate and 0.2 ml of 100 mM Tris-HCl (pH 7.8)/0.1 mM acetyl CoA/0.4 mg/ml 5, 5'-dithiobis-2-nitrobenzoic acid/0.1 mM chloramphenicol was added. After 15 min the absorbance at 412 nm was determined by a microplate reader (Molecular Devices Corp.)

For isolation of the desired protein (CAT in the present example) in a purified form, conventional isolation and purification techniques are employed. Such techniques include centrifugation, filtration, chromatography, electrophoresis, dialysis and the like well known to one of ordinary skill in the art.

RESULTS

Effect of ECMV UTR on CAT Expression

In order to determine whether the EMCV UTR would confer enhanced and capindependent translation to the predominantly uncapped transcripts made by bacteriophage T7 RNA polymerase, encoded by vaccinia virus, in mammalian cells, two plasmids, pT7CAT and pT7EMCAT, were constructed. Each contained the T7 010 promoter and the CAT gene but the latter also had a segment of the ECMV UTR, corresponding to nucleotides 163 to 746 of the EMCV UTR downstream of the T7 RNA start site as shown in FIG. 1. CAT activity was measured 24 hr after transfection of each T7 promoter plasmid into cells that had been infected with the helper virus vTF7-3 (Fuerst et al, supra), which express the T7 RNA polymerase. An approximately 7-fold enhancement provided by the EMCV UTR was reproduced in several independent experiments. CAT level expressed by a T7EMCAT plasmid which did not contain the T7 stem-loop was 10 fold less than T7EMCAT indicating that the T7 stem-loop is necessary for expression despite the fact that EMCV UTR is expected to have considerable secondary structure. Both pT7CAT and pT7EMCAT contain vaccinia virus thymidine kinase sequences flanking the expression cassette making it simple to generate recombinant vaccinia viruses vT7CAT and vT7EMCAT. CAT expression was measured after infecting cells simultaneously with either T7 promoter-containing recombinant virus and vTF7-3 (to provide T7 RNA polymerase). The overall results were similar to those obtained by transfection with the corresponding plasmids except that the EMCV UTR enhanced expression 4- to 5-fold in repeated experiments.

Effects of Hypertonic Medium on Expression

Figure 2:
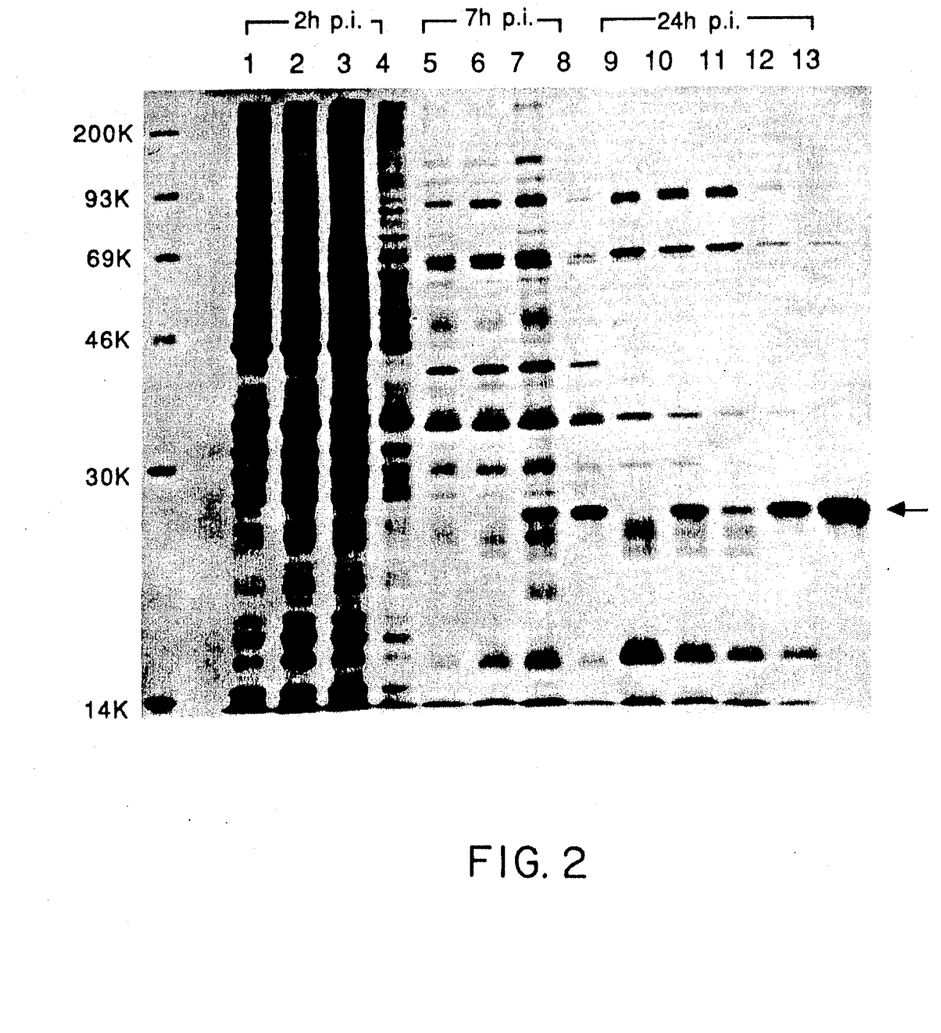

In order to determine the effect of hypertonicity on CAT expression, CV-1 cells were infected with vTF7-3 to provide T7 RNA polymerase and either vT7CAT or vT7EMCAT. Protein synthesis was monitored by NaDodSO$_4$-polyacrylamide gel electrophoresis of cytoplasmic proteins from cells labeled with [$^{35}$S]methionine at various times after infection in isotonic or hypertonic (190 mM) medium (FIG. 2). At 2 hr after infection, predominantly host proteins were labeled under all conditions (lanes 1-4). However, by 6 hr. host protein synthesis was inhibited and the late pattern of protein synthesis was established (lanes 5-8). A band, corresponding in size to the CAT polypeptide, was clearly seen in the autoradiogram of proteins from cells infected with vT7EMCAT (lane 7) but was hardly detected in the proteins from cells infected with vT7CAT (lane 6) and missing from control cells infected with wild-type vaccinia virus (not shown). Moreover, under hypertonic conditions, there was an absolute increase in labeling of CAT and a decrease in labeling of vaccinia viral late proteins, in cells infected with vT7EMCAT (lane 8). At still later times, CAT expressed by vT7CAT was readily detected as a prominent band (lane 10) of similar intensity to that of the major viral proteins (lane 9). At this time, however, the CAT protein was the predominant band expressed by vT7EMCAT under isotonic conditions (lane 12) and was even more dominant under hypertonic conditions (lane 13). Densitometer tracings of the fluorogram indicate that at 24 hr, 78% of the [$^{35}$S]methionine was incorporated into CAT.

Figure 3A:
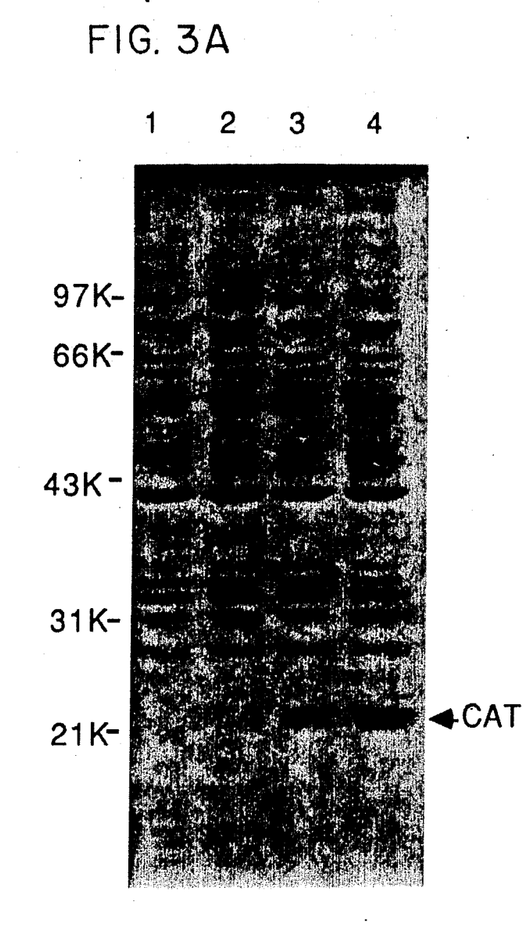
FIGS. 3A and B demonstrate the accumulation of CAT protein by 24 hr after infection. CV-1 cell monolayers were infected with 20 PFU per cell of wild-type vaccinia virus (A, lane 1; B, solid bar), or co-infected with vTF7-3 and vT7CAT (A, lane 2; B, hatched bar), or co-infected with vTF7-3 and vT7EMCAT (a, lanes 3 and 4; B, open bar) at a multiplicity of 10 PFU per cell for each virus. At 4 hr after infection, the isotonic medium was maintained (A, lanes 1-3; B, part 1) or changed to 190 mM (hypertonic) NaCl (A, lane 4; B, part 2). At 24 hr after infection, cell lysates were prepared, 20 μg of protein were loaded in each lane of a 10% NaDodSO$_4$-polyacrylamide gel and following electrophoresis the gel was stained with Coomassie brilliant blue (A) or CAT activity was determined as described in the text.
Figure 3B:
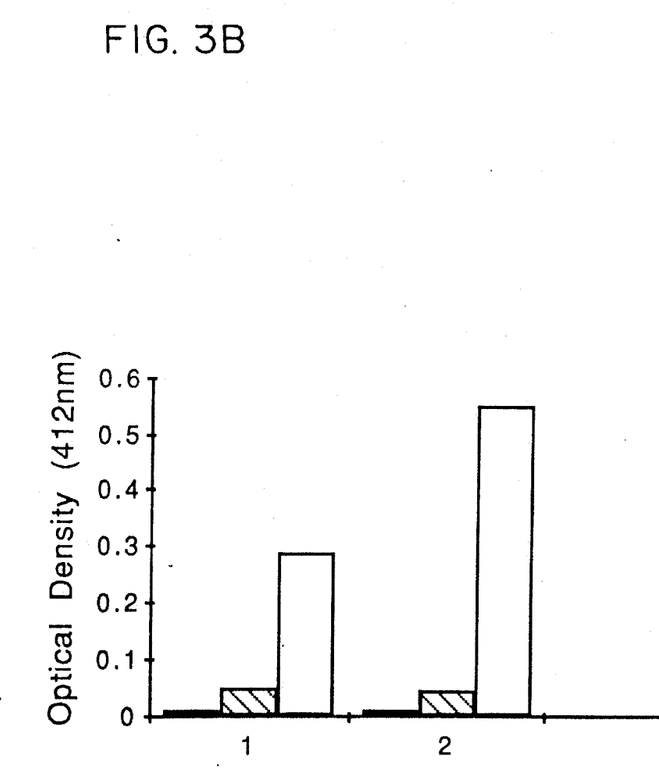

The total accumulation of CAT protein at 24 hr after infection was determined by Coomassie brilliant blue staining of NaDodSO$_4$-polyacrylamide gels as well as by assaying CAT activity (FIG. 3). Cells were co-infected in isotonic medium and then either maintained under these conditions or were transferred to hypertonic medium after 4 hr. After a total of 24 hr, the cells were lysed and 20 μg of cytoplasmic protein were loaded on each lane of a 10% polyacrylamide gel. Following electrophoresis, densitometry of the Coomassie brilliant blue stained gel revealed that the CAT protein comprised 2% or 7% of the total protein when expressed from vT7CAT or vT7EMCAT under isotonic conditions, respectively and 10% of the total protein when expressed from vT7EMCAT in hypertonic conditions (FIG. 3A). The selective effect of hypertonicity on EMCV UTR-mediated expression was confirmed by measurements of CAT activity in extracts prepared from cells at 24 hr after co-infection (FIG. 3B). CAT activity was 10-fold higher when expressed from vT7EMCAT in hypertonic medium as compared to the expression level from vT7CAT.

Effect of EMCV UTR on in Vitro Translation Properties of T7 Transcripts

Figure 4:
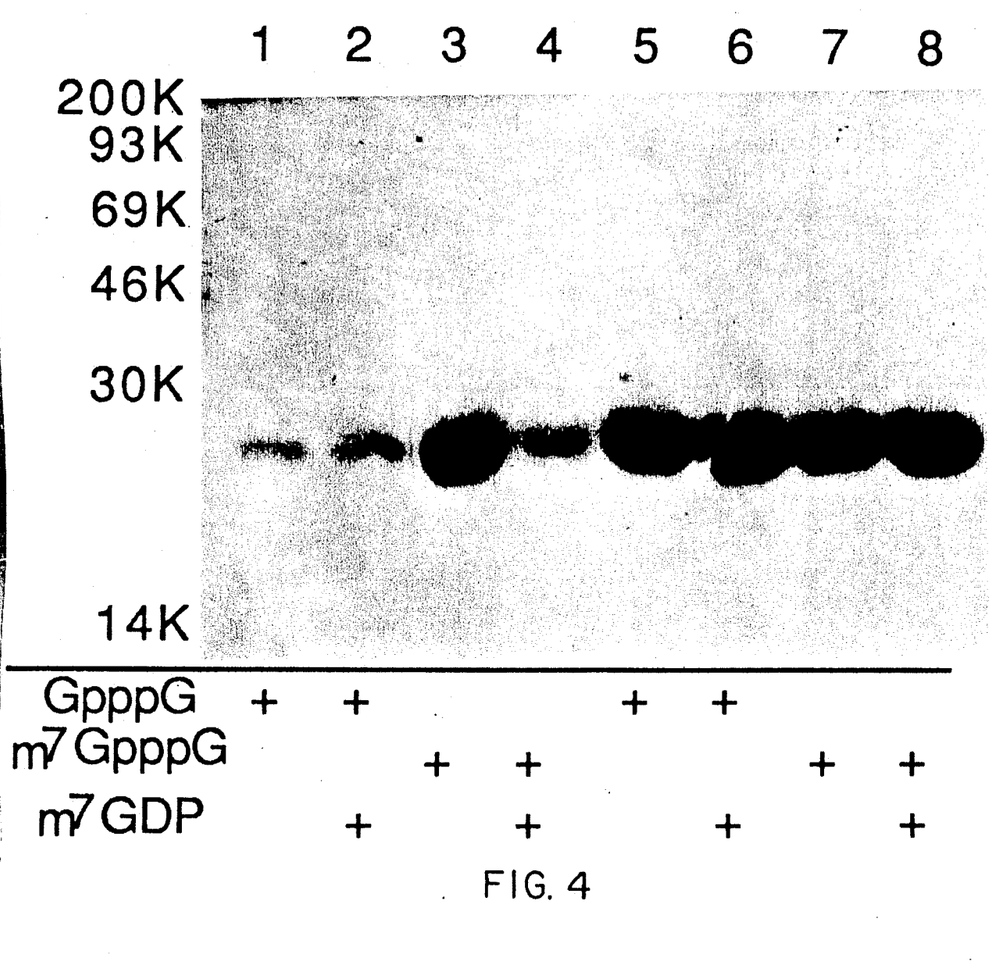
FIG. 4 shows cap-independent translation of RNA containing EMCV UTR. In vitro transcription was carried out using Bam HI digested pT7CAT (lanes 1-4) or pT7EMCAT (lanes 5-8) as templates. Lanes containing unmethylated (GpppG) or methylated (m$^7$GpppG) capped RNA are indicated. Translation in micrococcal-treated rabbit reticulocyte lysate was performed with RNA concentration of 8 nM with or without the presence of 0.1 mM methylated GDP (m$^7$GDP) as indicated.

To further investigate the mechanism by which the EMCV UTR had elevated the expression of the presumably uncapped T7 transcripts in vivo, we synthesized RNAs with and without m$^7$G capped 5'-ends and compared their in vitro translation properties. Bacteriophage T7 RNA polymerase was used to transcribe the plasmids pT7CAT and pT7EMCAT (FIG. 1) in order to prepare mRNAs with and without the EMCV UTR. Transcripts containing 5' methylated caps were generated by adding high concentrations of m$^7$GpppG to the transcription reaction; GpppG was added to parallel reactions to generate unmethylated caps which are known to be non-functional in translation but may also protect the RNAs against exonuclease degradation. These transcripts were translated in a rabbit reticulocyte lysate in the presence or absence of the cap analog m$^7$GDP, known to be a specific inhibitor of methylated capped mRNA translation in vitro. In the absence of the EMCV UTR, translation of T7-CAT transcripts was found to be methylated cap-dependent as the GpppG-terminated RNA was inefficiently translated relative to that of m$^7$GpppG-terminated RNA (FIG. 4). Moreover, translation of m$^7$GpppG-terminated RNA was inhibited by m$^7$GDP (FIG. 4). In contrast, the translation of T7-EMCV UTR-CAT transcripts was highly efficient regardless of 5' cap structure and was insensitive to m$^7$GDP as well, indicating that the EMCV UTR-containing mRNAs were translated in a cap-independent fashion. The specificity of m$^7$GDP was further demonstrated by simultaneously translating capped transcripts, with and without EMCV UTRs, that encode different length polypeptides; only those without the EMCV UTR were inhibited (data not shown).

Association of T7 Transcripts with Polyribosomes

Figure 5A:
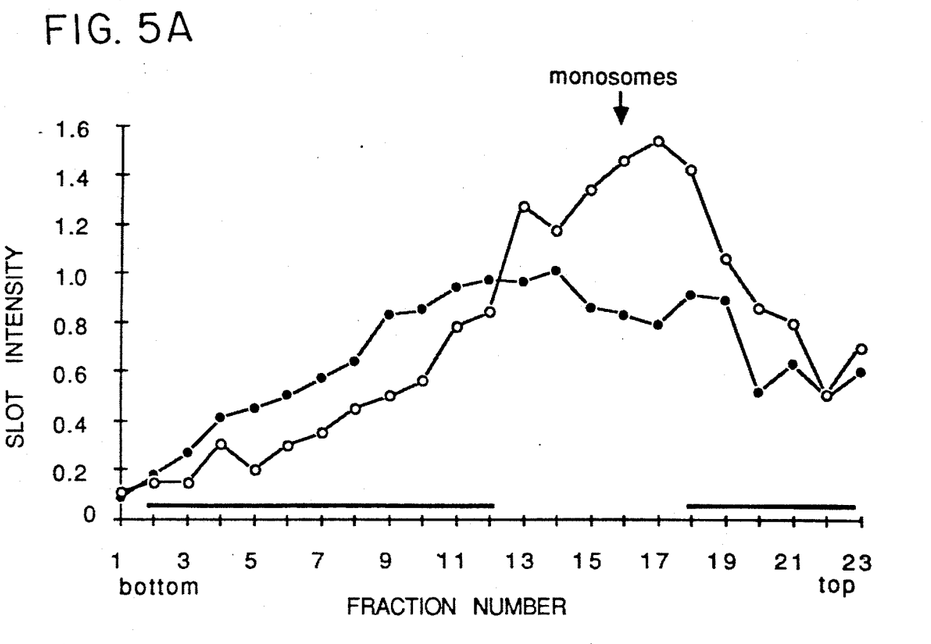
FIGS. 5A and B demonstrates polyribosome-association and invitro translation of CAT RNA made in infected cells. (A) HeLa cells were co-infected with 10 PFU/cell of vTF7-3 and 10 PFU/cell of either vT7CAT (•—•) or vT7EMCAT (0—0). After 12 hr, cytoplasmic extracts were prepared and sedimented on sucrose density gradients. Optical density at 260 nm of each fraction was measured and the position of the monosome peak is indicated. A 20 μl sample of each fraction was immobilized on nitrocellulose using a slot blot apparatus and then hybridized to a [$^{32}p$]-CAT probe. Autoradiograms were made and the intensities of the bands were determined by densitometry. Indicated fractions (horizontal lines) were pooled and processed for in vitro translation. (B) Samples (1 μg) of the pooled RNA were translated in a rabbit reticulocyte lysate in a final reaction volume of 12.5 μl with (+) or without (−) 0.1 mM m$^7$GDP as indicated. The translation products of no RNA (lane 1), polyribosome associated T7-CAT RNA (lanes 2, 3), polyribosome-associated T7 EMCV UTR-CAT RNA (lanes 4, 5), free T7-CAT RNA (lanes 6, 7), free T7EMCV UTR-CAT RNA (lanes 8, 9) were analyzed by NaDodSO$_4$-polyacrylamide gel electrophorese and a fluorogram was made.

If the beneficial effect of the EMCV UTR were due to more efficient translation of uncapped messages, as the in vitro studies had suggested, than a higher percentage of such transcripts should be polyribosome-associated relative to that of T7 transcripts lacking the UTR. To evaluate this, Hela cells were co-infected with vTF7-3 and either vT7CAT or vT7EMCAT and 12 hr later cytoplasmic extracts were prepared and subjected to sucrose density gradient centrifugation. The monosomes peak was located by optical density measurements and the distribution of CAT mRNA along the gradient was determined by hybridization of a sample of each fraction with a [$^{32}p$]-CAT probe. Autoradiograms were made of the "slot-blot" hybridizations and the intensity of each slot was measured by densitometry. These data, compiled in FIG. 5A, revealed that there were similar total amounts of T7-EMCV UTR-CAT RNA and T7-CAT RNA but that a larger fraction of the former was associated with disomes and heavier polyribosomes.

Figure 5B:
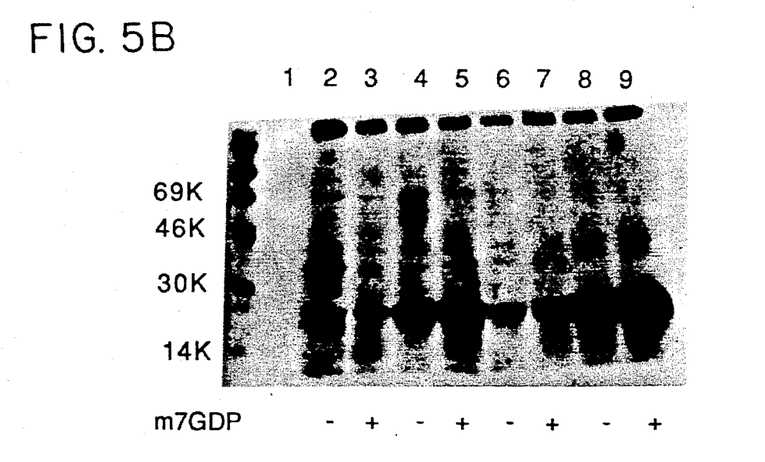

The polyribosome-associated and the free CAT RNA were pooled separately and translated in rabbit reticulocyte lysates in the presence or absence of m7GDP. Inspection of fluorograms of NaDodSO$_4$-polyacrylamide gels (FIG. 5B) led to several significant findings. First, both the polyribosome-bound and free T7-EMCV UTR-CAT RNA was translated more efficiently than either T7-CAT RNA fraction. Second, translation of the polyribosome-bound T7-CAT RNA was inhibited by m$^7$GDP whereas the corresponding free RNA was not inhibited. Third, translation of neither the polyribosome nor the free T7 EMCV UTR-CAT RNA was inhibited by m$^7$GDP. Without being bound to any specific theory, these observations were interpreted as follows. The small amounts of capped T7-CAT transcripts were selectively associated with the polyribosome fraction accounting for the inhibition of their translation by m$^7$GDP. The free T7-CAT RNA was mostly uncapped but owing to the large amount it was translated, albeit inefficiently, and in a cap-independent manner. The cap-status of the T7 EMCV UTR-CAT RNA could not be judged since our in vitro studies had shown that neither capped nor uncapped forms are inhibited by m$^7$GDP. However, since the 5' ends of the T7-CAT and T7-EMCV UTR-CAT transcripts contain the identical 5' end and stem-loop structure, there is no reason to assume that they would be differentially capped.

Studies have indicated that the effective utilization of prokaryotic transcription components in a eukaryotic cell raises a number of potential problems, the solution of which may provide not only a superior expression system, but also could contribute to the understanding of eukaryotic RNA structure/function relationships. The bacteriophage T7 transcription system, or similar ones from related bacteriophages, offer advantages that have been previously enumerated (Fuerst et al, supra). By choosing a vaccinia virus vector, which replicates in the cytoplasm, extra difficulties associated with nuclear processing and transport were avoided. Although vaccinia virus has its own capping and methylating enzymes (Wei et al, 1974, *Proc. Natl. Acad. Sci. USA* 71, 3014-3018), RNA made by T7 RNA polymerase is not as efficiently capped as RNAs made by the vaccinia virus polymerase (Fuerst et al, supra). Since the cap is needed for both RNA stability and translation [Grifo et al, 1982, in *Interaction of Translational & Transcriptional Controls in the Regulation of Gene Expression* eds. Grunberg-Manago, M. & Safer, B., (New York: Elsvier Biomedical), pp. 359-372], this deficiency presented a severe challenge. The RNA stability problem, however, was solved by retaining the T7 stem-loop segment at the 5' ends of the transcripts. This stem-loop, nevertheless, may have exacerbated the capping problem since in vitro studies indicated that RNA containing this structure was a poorer substrate for the vaccinia RNA guanylyl transferase (Fuerst et al, supra). In addition, the stem-loop structure might interfere with ribosome scanning (Pelletier et al, 1985, Cell 40, 515-526; Kozak, M., 1980, Cell 19, 79-90). Nevertheless, owing to the enormous amount of stable RNA generated (approximately 30% of the total cytoplasmic RNA), useful amounts of protein were made with the vaccinia/T7 hybrid expression system.

It is important to point out here that at the start of the present study, the applicants did not know whether the EMCV UTR could function in a eukaryotic cell when attached to an RNA made by a prokaryotic transcription system. Further more, since vaccinia virus inhibits host cell protein synthesis, it was a matter of concern that the changes in the protein synthesis machinery of the cell caused by vaccinia virus might prevent the efficient use of the EMCV UTR. Hence, when it was found that not only did the EMCV UTR system of the present invention function in the eukaryotic system, but it also enhanced the level of protein made by 500% or more, it was indeed quite unexpected and represented a major improvement in gene expression technology.

The mammalian cell expression system of the present invention is truly eclectic in that the vector is a DNA virus, the RNA polymerase and promoter are derived from a DNA bacteriophage, and the ribosome binding site is from an RNA virus. Nevertheless, the system provides a powerful, rapid, versatile and simple way of expressing genes in mammalian or avian cells. It may be used most simply by transfecting a plasmid containing a T7 promoter regulated gene of interest into cells that have been infected with a standard recombinant vaccinia virus expressing T7 RNA polymerase. In the latter approach, there is no need to prepare a new recombinant vaccinia virus. Alternatively, by recombining the T7 promoter regulated gene into vaccinia virus and using a standard double infection protocol, larger numbers of cells may be conveniently used and still higher expression may be obtained. Results with the small 25,000 dalton CAT protein, usually chosen for model studies, revealed that it was the dominant polypeptide made in vaccinia virus-infected cells and after only 24 hr accumulated to a level of 16.5 $\mu$g per $2 \times 10^6$ cells which accounted for approximately 10% of the Coomassie brilliant blue stained protein on polyacrylamide gels. The level of expression with the vaccinia/T-7/EMCV hybrid system is greater than that obtained with conventional vaccinia virus vectors even when the strongest poxvirus promoters described thus far are used (Falkner, et al, 1988, *J. Virol.* 62, 1849–1854; Patel et al, 1988, *Proc. Natl. Acad. Sci. USA* 85, 9431–9435). The vaccinia hybrid system has other advantages, such as use for potentially toxic genes, since expression does not occur until cells are co-infected with the T7 RNA polymerase containing helper virus. Thus, the expression of toxic genes to kill target cells can be controlled by this unique feature of the present invention.

Of course, having demonstrated the operability of the present invention with the model CAT system, it is clear that the expression of other proteins is achieved similarly, as will be suggested to one of ordinary skill in the art.

It is noted that the embodiments described herein are for illustrative purposes only and that various modifications in light thereof will be suggested to persons skilled in the art and are to be included within the spirit and purview of this application and scope of the appended claims.

What is claimed is:

1. A method for synthesizing protein, comprising:
   (a) infecting a mammalian cell with a recombinant cytoplamic DNA virus the genome of which includes the following elements operably linked 5' to 3': a promoter, wherein said promoter is selected from the group consisting of T7, SP6, T3, and GH1 promoters, followed by a cDNA copy of an untranslated region of a cardiovirus RNA that confers cap-independent translation, followed by a gene encoding a protein desired to be expressed, said promoter, cDNA and the gene being so arranged that said gene is efficiently expressed in a mammalian cell infected with said recombinant virus only when said cell contains an RNA polymerase active with said promoter; and
   (b) infecting said cell with a second cytoplasmic DNA virus that expresses said RNA polymerase so that said protein is expressed in the cell; and then
   (c) recovering the desired protein by suitable isolation and purification techniques.

2. The method of claim 1, wherein said cardiovirus is EMCV.

3. The method of claim 1, wherein said promoter and RNA polymerase are from T7.

4. The method of claim 1, wherein said cytoplasmic DNA virus is vaccinia.

5. The method of claim 1 further exposing said cell to hypertonic conditions.

6. The method of claim 1 wherein said gene is a toxic gene.

7. A method for synthesizing protein, which comprises transfecting a mammalian cell with a recombinant plasmid comprising the following elements operably linked 5' to 3;: a promoter, wherein said promoter is selected from the group consisting of T7, SP6, T3, and GH1 promoters, followed by a cDNA copy of an untranslated region of a cardiovirus RNA that confers cap-independent translation, followed by a gene encoding a protein desired to be expressed, said promoter, cDNA and the gene being so arranged that said gene is efficiently expressed in a mammalian cell transfected with said recombinant plasmid only when said cell contains RNA polymerase active with said promoter; and infecting said cell with a DNA based cytoplasmic virus expressing said RNA polymerase so that said protein is expressed in said cell; and then recovering the desired protein by suitable isolation and purification techniques.

8. The method of claim 7, wherein said cardiovirus is EMCV.

9. The method of claim 7, wherein said promoter and RNA polymerase are from T7.

10. The method of claim 7, wherein said cytoplasmic DNA virus is vaccinia.

11. The method of claim 7 further exposing said cell to hypertonic conditions.

12. The method of claim 7 wherein said gene is a toxic gene.